United States Patent [19]

Godfried Andre Van Kruchten

[11] Patent Number: 6,137,014
[45] Date of Patent: *Oct. 24, 2000

[54] CATALYTIC HYDROLYSIS OF ALKYLENE OXIDES

[75] Inventor: Eugene Marie Godfried Andre Van Kruchten, Amsterdam, Netherlands

[73] Assignee: Shell Oil Company, Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 09/182,920

[22] Filed: Oct. 30, 1998

[30] Foreign Application Priority Data

Oct. 30, 1997 [EP] European Pat. Off. ............. 97203368

[51] Int. Cl.$^7$ .................................................. C07L 27/00
[52] U.S. Cl. ............................................................ 568/867
[58] Field of Search ............................................... 568/867

[56] References Cited

U.S. PATENT DOCUMENTS

| | | | |
|---|---|---|---|
| 3,997,562 | 12/1976 | Liotta | 260/338 |
| 4,160,116 | 7/1979 | Mieno et al. | 568/867 |
| 4,645,817 | 2/1987 | Probst et al. | 528/45 |
| 4,822,925 | 4/1989 | Briggs | 556/20 |
| 4,943,375 | 7/1990 | Bradshaw et al. | 216/674 |
| 4,982,021 | 1/1991 | Best | 568/867 |
| 5,003,111 | 3/1991 | Harper | 568/618 |
| 5,488,184 | 1/1996 | Reman | 568/867 |

FOREIGN PATENT DOCUMENTS

| | | |
|---|---|---|
| 0000218 | 1/1979 | European Pat. Off. . |
| 0013444 | 7/1980 | European Pat. Off. . |
| 0156449 A2 | 10/1985 | European Pat. Off. . |
| 0159643 B1 | 10/1985 | European Pat. Off. . |
| 57-139026 | 8/1982 | Japan . |
| 2001901 C1 | 10/1993 | Russian Federation . |
| WO 95/20559 | 8/1995 | WIPO . |
| WO 97/19043 | 5/1997 | WIPO . |
| WO 98/02404 | 1/1998 | WIPO . |

OTHER PUBLICATIONS

"Separation and Preconcentration of Strontium From Biological, Environmental, and Nuclear Waste Samples by Extraction Chromatography Using a Crown Ether," by E. P. Horwitz, M. L. Dietz, and D. E. Fisher, *Analytical Chemistry*, vol. 63, No. 5, Mar. 1, 1991, pp. 522–525.

"Darstellung Und Eigenschaften Von Austauschern Auf Basis Von Kronenverbindungen," by E. Blasius, W. Adrian, K. P. Janzen, and G. Klautke, *Journal of Chromatography*, 96 (1974) pp. 89–97.

"Cation Binding Properties of Poly(Vinyl Macrocyclic Polyethers)," by S. Kopolow, T. E. Hogen Esch, J. Smid, *Macromolecules*, vol. 4, No. 3, May–Jun. 1971, pp. 359–360.

"Poly(Vinyl Macrocyclic Polyethers). Synthesis and Cation Binding Properties," by S. Kopolow, T. E. Hogen Esch, and J. Smid, Macromolecules, vol. 6, No. 1, Jan.–Feb. 1973, pp. 133–142.

"Macroheterocyclic Ligands on Polymers," by J. Smid and R. Sinta, Host Guest Complex Chemistry III, Springer–Verlag 1984, pp. 106–157.

International Search Report of Mar. 17, 1999.

*Primary Examiner*—Michael L. Shippen

[57] ABSTRACT

A process for the preparation of alkylene glycols by reacting an alkylene oxide with water in the presence of a catalytic composition comprising a macrocyclic chelating compound complexed with an ionic compound the anion of which is catalytically effective under the reaction conditions. Preferably, the macrocycle is a crown ether or a cryptate and the anion is selected from the group of halogenides, carboxylates having from 1–20 carbon atoms, hydrogen carbonate, hydrogen sulphite, hydrogen phosphate and metalates.

7 Claims, No Drawings

CATALYTIC HYDROLYSIS OF ALKYLENE OXIDES

FIELD OF THE INVENTION

The present invention relates to a process for the preparation of alkylene glycols by reacting an alkylene oxide with water in the presence of a catalytic composition.

BACKGROUND OF THE INVENTION

Alkylene glycols, in particular monoalkylene glycols, are of established commercial interest. For example, monoalkylene glycols are being used in anti-freeze compositions, as solvents and as base materials in the production of polyalkylene terephthalates e.g. for fibres or bottles.

The production of alkylene glycols by liquid phase hydrolysis of alkylene oxide is known. The hydrolysis is performed without a catalyst by adding a large excess of water, e.g. 20 to 25 moles of water per mole of alkylene oxide, or with a smaller excess of water in a catalytic system. The reaction is considered to be a nucleophilic substitution reaction, whereby opening of the alkylene oxide ring occurs, water acting as the nucleophile.

Because the primarily formed monoalkylene glycol also acts as a nucleophile, as a rule a mixture of monoalkylene glycol, dialkylene glycol and higher alkylene glycols is formed. In order to increase the selectivity to monoalkylene glycol, it is necessary to suppress the secondary reaction between the primary product and the alkylene oxide, which competes with the hydrolysis of the alkylene oxide.

One effective means for suppressing the secondary reaction is to increase the relative amount of water present in the reaction mixture. Although this measure improves the selectivity towards the production of the monoalkylene glycol, it creates a problem in that large amounts of water have to be removed for recovering the product.

Considerable efforts have been made to find an alternative for increasing the reaction selectivity without having to use a large excess of water. Usually these efforts have focused on the selection of more active hydrolysis catalysts and various catalysts have been disclosed.

Both acid and alkaline hydrolysis catalysts have been investigated, whereby it would appear that the use of acid catalysts enhances the reaction rate without significantly affecting the selectivity, whereas by using alkaline catalysts generally lower selectivities with respect to the monoalkylene glycol are obtained.

Certain anions, e.g. bicarbonate (hydrogen carbonate), bisulphite (hydrogen sulphite), formate and molybdate are known to exhibit good catalytic activity in terms of alkylene oxide conversion and selectivity towards monoalkylene glycol. However when the salts of these anions are used as the catalyst in a homogeneous system, work-up of the reaction product by distillation will pose a problem because the salts are poorly soluble in the glycol and tend to make it semisolid.

High conversions, good selectivity and a low water/alkylene oxide ratio can be obtained with the process, disclosed in EP-A 0 156 449. According to this document, the hydrolysis of alkylene oxides is carried out in the presence of a selectivity-enhancing metalate anion-containing material, preferably a solid having electropositive complexing sites having affinity for the metalate anions. The said solid is preferably an anion exchange resin, the metalate anions are specified as molybdate, tungstate, metavanadate, hydrogenpyrovanadate and pyrovanadate anions. A complication of this process is that the alkylene glycol-containing product stream also comprises a substantial amount of metalate anions, displaced from the electropositive complexing sites of the solid metalate anion containing material. In order to reduce the amount of metalate anions in the alkylene glycol product stream, this stream is contacted with a solid having electropositive complexing sites associated with anions which are replaceable by the said metalate anions.

It has been proposed to simplify the product recovery procedure by using water-insoluble vanadate and molybdate salts. However, with these metalate anion salts the obtained selectivities are significantly lower than with the water-soluble metalates.

In JP-A-57-139026 there is disclosed a method for reacting alkylene oxide with water in the presence of a halogen type anion exchange resin and in the co-presence of carbon dioxide.

In RU-C-2001901 it is pointed out that the former disclosure has the disadvantage of the formation of carbonates in the reaction mixture which are difficult to separate from the glycols on account of the closeness of their boiling points. This patent publication discloses as its invention the performance of the alkylene oxide hydrolysis reaction in one or a sequence of 'extrusion reactor(s)' (continuous reaction), in the presence of 'anionite' (anion exchange resin of the quaternary ammonium type) in bicarbonate form and carbon dioxide. The essential difference with the former, Japanese, patent publication appears to be the use of the bicarbonate form of the anion exchanger instead of the halogen form thereof. And yet, the Russian patent does not dispense with the addition of carbon dioxide to the feed.

According to WO 95/20559, the presence of carbon dioxide in the feed is detrimental to the catalytic effect of bicarbonate-exchanged resins of the quaternary ammonium type. In this document there is disclosed a process for the preparation of alkylene glycols wherein an alkylene oxide is reacted with water in the presence of a catalyst composition comprising a solid material having one or more electropositive sites, which are coordinated with one or more anions other than metalate or halogen anions, with the proviso that when the solid material is an anionic exchange resin of the quaternary ammonium type and the anion is bicarbonate the process is performed in the substantial absence of carbon dioxide.

A drawback shared by the conventional anionic exchange resins is their limited tolerance to heat. In practising the process of alkylene oxide hydrolysis according to WO 95/20559 with catalyst compositions based on conventional organic quaternary ammonium ion exchangers it has been found, that under severe reaction conditions (high temperature and/or long service) the selectivity of the conventional resin-based catalysts tends to deteriorate strongly while their activity is even enhanced.

Macrocyclic chelating compounds are known—see for example J. March in Advanced Organic Chemistry; Reactions, Mechanisms and Structures, $4^{th}$ Edition 1992, pp 82–87 and 363–364. They have the property of forming complexes with positive ions (cations), although they can also complex neutral molecules. They have a regular organic ring structure containing a plurality of heteroatoms such as oxygen, nitrogen or sulphur. They can be monocyclic, bicyclic or cycles of a higher order. The bonding of cations in these complexes is the result of ion-dipole attractions between the heteroatoms and the positive ions. Thus, the number of the heteroatoms in the molecule determines the binding strength and the size and shape of the cavity determines the ions (or neutral molecules) which can be bound. The macrocycle is called the host and the ion is the guest. Owing to their shape and size, the ability of the host molecules to bind guests is often very specific, enabling the host to pull just one cation or molecule out of a mixture.

The best known macrocyclic chelating compounds are those wherein all or most of the heteroatoms are oxygen, in particular the crown ethers wherein the ring structure is two-dimensional (monocyclic) and the cryptands wherein the ring structure is three-dimensional (bicyclic, tricyclic etc.). When the cavity of the macrocycle is spherical the molecule is called spherand. Other more exotic types are the calixarenes, cryptophanes, hemispherands and pondands.

Crown ethers are usually denoted by their total number of atoms and number of heteroatoms in the ring, plus substituents when present. Examples are 12-crown-4 (I), 15-crown-5 (II) and dicyclohexano-18-crown-6 (III). An example of a calixarene is 4 tert-butylcalix(4)arene (V).

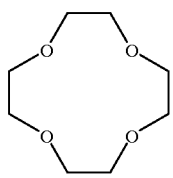

(I)

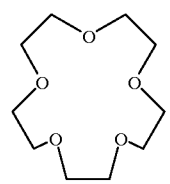

(II)

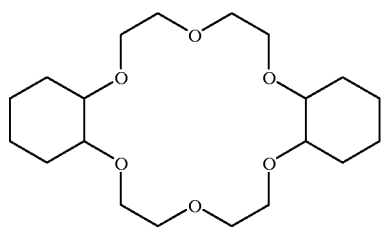

(III)

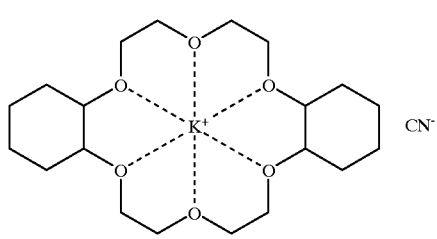

(IV)

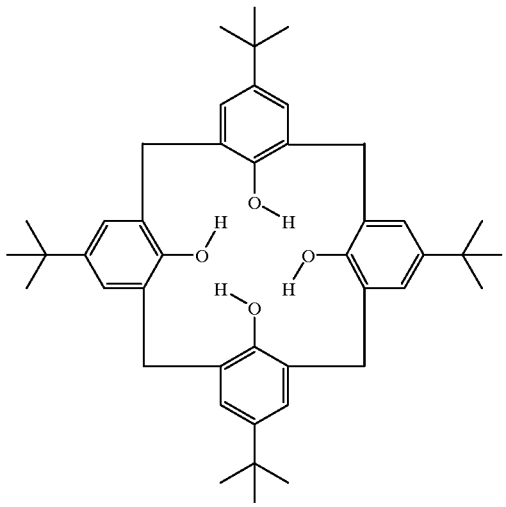

(V)

Crown ethers have been used as phase transfer catalysts, i.e. for getting a reactant anion of a hydrophylic compound into the organic phase where it can react with a substrate. For example, a salt like KCN is converted by dicyclohexano-18-crown-6 into a new salt (IV), whose anion CN⁻ is the same but whose cation is much larger, having its positive charge spread over a large volume and hence much less concentrated. This larger cation is much more attracted to organic solvents. Though KCN is generally insoluble in organic solvents, its crown ether complex is soluble in many of them, making its reactions in the organic phase possible.

In U.S. Pat. No. 4,645,817, equivalent of EP-B 0 159 643, there is disclosed a process for the preparation of a hydroxyl group containing alkoxylation product of an organic carboxylic acid, which process comprises reacting an organic compound containing at least one carboxyl group with an alkylene oxide in an alkoxylation reaction in the presence of a phase transfer catalyst. The catalyst may comprise a basic alkali metal compound which has undergone crown ether complex formation. Here the crown ether is used to phase transfer the basic alkali metal alkoxylation catalyst.

SUMMARY OF THE INVENTION

It has now been found that, independently from any inherent catalytic or phase-transferring effect of the macrocyclic chelating compounds, they can be complexed to good effect with alkylene oxide hydrolysis catalysts in homogeneous as well as in heterogeneous systems. In homogeneous systems they provide the advantage of easier separation and recirculation and in heterogeneous systems they provide the advantage of much greater thermal stability than anything known before.

The invention therefore provides a process for the preparation of alkylene glycols by reacting an alkylene oxide with water in the presence of a catalytic composition comprising a macrocyclic chelating compound complexed with an ionic compound the anion of which is catalytically effective under the reaction conditions.

DETAILED DESCRIPTION OF THE INVENTION

The macrocyclic chelating compound is preferably selected from the group of crown ethers and cryptands.

The catalytically effective anion is preferably selected from the group of halogenides, carboxylates having from 1–20 carbon atoms, hydrogen carbonate, hydrogen sulphite, hydrogen phosphate and metalates.

The cation may suitably be that of an alkali metal, an alkaline earth metal or ammonium. The choice of the cation is not critical for the catalytic effect of the anion. On the other hand, since every macrocyclic compound is selective for one or a very limited number of cations, the choice of the cation will determine the choice of the macrocyclic compound(s) which should preferably be used. Thus, when the cation is sodium or calcium a suitable crown ether is 15-crown-5 (1,4,7,10,13-pentaoxacyclopentadecane), with lithium it is either 15-crown-5 or 12-crown-4 (1,4,7,10-tetraoxacyclododecane) and with potassium it is 18-crown-6 (1,4,7,10,13,16-hexaoxacyclooctadecane).

The amount of catalytic anion used in the process of the present invention will generally be between 0.001 and 1, preferably between 0.01 and 0.1, mol per mol of alkylene oxide present in the reactor.

It will be understood that the relative amount of macrocyclic chelating compound and ionic compound used to make up the catalytic composition will depend on the specific cation and anion chosen. Thus, when a monovalent cation is used with a monovalent anion the relative amount of macrocycle and catalytic anion will be suitably equimolar (1:1 mol). If however a divalent cation (e.g. $Ba^{2+}$) is used with a monovalent anion (e.g. formate; $HCOO^-$) the relative amounts of catalytic anion and macrocyclic chelating compound used is suitably 2:1 mol. And in certain situations—when one cation is held by more that one macrocyclic molecule—a molar excess of the macrocyclic compound will be preferred, e.g. to the ratio of 1:2 or 1:3 mol. Amounts of either the macrocycle or the anionic compound which are in excess of what is needed to form the catalytic composition are not particularly detrimental to the hydrolysis reaction, but they will have no advantage.

The complexes according to the invention may be prepared by simply adding their two components, i.e. the macrocyclic chelating compound and the salt, in the required respective concentration to a solvent in which both are soluble. Suitably, the solvent is water or ethylene glycol because water is a reactant in the ethylene oxide hydrolysis reaction and ethylene glycol is its product.

As stated above, when the complexes are used according to the present invention as ethylene oxide hydrolysis catalysts in a homogeneous reaction system their main advantage over non-complexed catalysts lies in the separation step following the reaction. In that case, this complexed homogeneous catalyst can be separated relatively easily because the complex is soluble in the feed as well as in the product. After separation, the complex can be recycled or it can be regenerated. For regeneration, the original macrocycle can be recovered, e.g. by absorption on acid-washed alumina or silica followed by elution with a volatile hydrocarbon, or with the help of a non-ionic compound which has a greater affinity to the particular macrocyclic compound. Examples of such non-ionic compounds are acetonitrile (U.S. Pat. No. 3,997,562), nitromethane (EP-B 0 013 444), dimethyl carbonate and dimethyl oxalate (EP-B 0 000 218). The macrocycle-nonionic bond can be broken by flashing (distilling at reduced pressure) the nonionic compound off, leaving the pure macrocycle.

As also stated above, when the complexes according to the invention are used in a heterogeneous system, i.e. on an inert support, their main advantage is a much greater thermal stability than that of the ion exchange resin type.

Therefore, in an important aspect of the present invention the complexed catalysts are immobilised on or incorporated in an inert solid support material. Preferably, the support material is selected from the groups of inorganic oxides and organic polymers. Preferable examples of inorganic oxides are silica, alumina, titania and zirconia. Preferable examples of organic polymers are the polystyrenes and the polyacrylates. Various copolymers and polycondensates can also be used as the inert solid support material.

A method of immobilising macrocycles and in particular crown ethers by loading them on resins such as AMBERLITE XAD-7 and AMBERCHROM CG-71ms is described in Anal. Chem. 63, 1991, 522–525 by E. P. Horwitz et al (AMBERLITE and AMBERCHROM are trademarks). A method for covalently bonding macrocycles such as crown ethers to silica gel is described in U.S. Pat. No. 4,943,375.

Methods of incorporating macrocycles in polymers were summed up by S. Smid and R. Sinta in a review article entitled "Macroheterocyclic Ligands on Polymers" in Topics of Current Chemistry, ed. F. L. Boschke, Springer Verlag Berlin Vol. 121, 1984, 105–156. Methods for the incorporation of crown ethers in a polymeric network by polycondensation with formaldehyde are described in J. Chromatography 97, 1974, 89–97 by E. Blasius et al. and in Anal. Chem. 62, 1990, 2283–2287 by T. Hayashita et al. Methods for the co-polymerisation of crown ethers with vinyl-type monomers such as styrene are described in J. Macromolecules 4, 1971, 359–360 and 6, 1973, 133–142 by S. Kopolow et al.

Custom-made immobilised crown ethers, on and in different solid support materials such as polystyrenes, acrylates and silicas, are presently being marketed under the tradename SuperLig by IBC Advanced Technologies Inc., American Fork, Utah, USA.

The catalyst composition according to the invention can be prepared by adding a solution of the ionic compound to the solid material containing the chelating macrocycle. For example, when the solid material is a polystyrene with a crown ether type of macrocycle and the catalytically active anion is formate, the catalyst composition may be prepared in a single step by adding to the solid support an aqueous solution of an alkali metal formate such as potassium formate, followed by washing with water.

The alkylene oxides, used as starting material in the process of the invention, have their conventional definition, i.e. they are compounds having a vicinal oxide (epoxy) group in their molecules.

Particularly suitable are alkylene oxides of the general formula

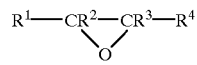

wherein $R^1$ to $R^4$ independently represent a hydrogen atom or an, optionally substituted, alkyl group having from 1 to 6 carbon atoms. Any alkyl group, represented by $R^1$, $R^2$, $R^3$ and/or $R^4$ preferably has from 1 to 3 carbon atoms. As substituents, inactive moieties, such as hydroxy groups may be present. Preferably, $R^1$, $R^2$ and $R^3$ represent hydrogen atoms and $R^4$ represents a non-substituted $C_1$–$C_3$-alkyl group and, more preferably, $R^1$, $R^2$, $R^3$ and $R^4$ all represent hydrogen atoms.

Examples of suitable alkylene oxides therefore include ethylene oxide, propylene oxide, 1,2-epoxybutane, 2,3-epoxybutane and glycidol. Ethylene oxide and propylene oxide are of particular commercial importance.

As mentioned above, it is advantageous to perform the hydrolysis of the alkylene oxides, without using excessive amounts of water. In the process according to the present invention, amounts of water in the range of 1 to 15 moles per mole of alkylene oxide are quite suitable, amounts in the range of 1 to 6 on the same basis being preferred. In the process of the invention high selectivities with respect to the monoalkylene glycol are often already achieved, when only 4 or 5 moles of water per mole of alkylene oxide are supplied.

The process of the invention may be carried out in batch operation. However, in particular for large scale embodiments it is preferred to operate the process continuously.

In order to obtain adequate time-yield values, it is recommended to perform the process under elevated temperature and pressure conditions.

Suitable reaction temperatures are generally in the range from 80 to 200° C., whereby temperatures in the range from 90 to 150° C. are preferred. The reaction pressure is usually selected in the range of 200 to 3000, preferably 200 to 2000 kPa. For batch operations of the process, the selected reaction pressure is advantageously obtained by pressurizing with an inert gas, such as nitrogen. If desired, mixtures of gases may be used, for example a mixture of carbon dioxide and nitrogen is in certain instances advantageous.

The following Examples will illustrate the invention.

EXAMPLES 1–16

Homogeneous Catalysts

A 250 ml autoclave was loaded with the catalyst (alkali metal salt or a mixture of alkali metal salt/crown ether) and water (100 g; 5.55 mol). The gascap was purged 3 times with nitrogen and an initial pressure of 900 kPa was employed. The mixture was heated to 100° C. Ethylene oxide (44 g; 1 mol) was slowly added under stirring (500 rpm). The reaction mixture was maintained under continuous stirring for 5 hours at 100° C. An end of run sample was taken for analysis by Gas Liquid Chromatography.

The results are summarised in the following Table 1.

TABLE 1

| Example No. | Catalyst | Amount of catalyst gram | Amount of catalyst mmol | EO conversion (%) | MEG selectivity (%) |
|---|---|---|---|---|---|
| Comp. 1 | — | — | — | 99.2 | 67.8 |
| Comp. 2 | sodium bicarbonate (NaHCO$_3$) | 2.52 | 30 | 99.7 | 85.0 |
| Comp. 3 | | | | 99.4 | 83.7 |
| 4 | NaHCO$_3$/18-crown-6 | 2.52/ 7.93 | 30/30 | 99.6 | 83.9 |
| Comp. 5 | potassium bicarbonate (KHCO$_3$) | 3.00 | 30 | 99.6 | 83.0 |
| 6 | KHCO$_3$/18-crown-6 | 3.00/ 7.93 | 30/30 | 99.4 | 81.9 |
| Comp. 7 | potassium formate (HCOOK) | 2.51 | 30 | 99.7 | 81.9 |
| 8 | HCOOK/18-crown-6 | 2.51/ 7.93 | 30/30 | 99.4 | 85.3 |
| Comp. 9 | potassium molybdate (K$_2$MoO$_4$) | 7.18 | 30 | 99.6 | 92.9 |
| 10 | K$_2$MoO$_4$/18-crown-6 | 7.18/ 15.87 | 30/60 | 99.2 | 95.0 |
| 11 | K$_2$MoO$_4$/18-crown-6 | 7.18/ 7.93 | 30/30 | 99.5 | 94.4 |
| 12 | barium formate [Ba(HCOO)$_2$] | 3.43 | 15 | 99.6 | 85.7 |
| 14 | HCOOK/tetra-t-butyl-calix (4) arene | 2.52/ 19.6 | 30/ 30.2 | 97.7 | 87.1 |
| 15 | lead formate [Pb(HCOO)$_2$] | 4.87 | 15 | 94.5 | 86.7 |
| 16 | Pb(HCOO)$_2$/18-crown-6 | 4.42/ 4.3 | 15/ 16.3 | 99.2 | 83.1 |

Work-up of Reaction Mixtures:

The crude reaction mixtures of Comparative Examples 2 and 3 wherein the catalyst was dissolved sodium bicarbonate, and of Example 4 wherein the catalyst was sodium bicarbonate complexed on crown ether, were evaporated at reduced pressure (90° C.; 1,5 kpa; about 60 minutes). After evaporation of the water, solid formation from the NaHCO$_3$ catalyst salt of Comparative Examples 2 and 3 occurred in the reaction mixtures. In contrast, the mixture resulting from Example 4 was homogeneous. Further evaporation (110° C.; 1,5 kPa; about 90 minutes) to remove MEG resulted in a thick unattractive slurry from Comparative Examples 2 and 3, while again the distillation residue from the crown ether catalysed products of Example 4 was completely homogeneous.

EXAMPLES 17–23

Heterogenous Catalysts (with macrocyclic complexing agent on solid support)

Catalyst Preparation

A complexing macrocycle immobilised on a solid support (silica) was obtained from IBC Advanced Technologies Inc. (American Fork, Utah, USA), viz Superlig 512-Silica (lot number 971230YK-4-56; capacity 0.23 mmol/g macrocycle). Both barium formate and lead formate were complexed on the Superlig.

Barium Formate Ba(HCOO)$_2$ on Superlig 512-silica.

70 G of Superlig 512 (silica; 16.1 mmol macrocycle) was added to a solution of 71.75 g (1 mol) of lithium formate hydrate (HCOOLi.H$_2$O), 5 g (0.02 mol) of barium formate [Ba(HCOO)$_2$] and 4 ml (0.1 mol) of formic acid (HCOOH) in 1 l of water. This mixture was gently stirred during 24 h. The solid catalyst was filtered, washed with water (3150 mol) and dried at 100° C. in a vacuum oven for 64 h. This resulted in a material containing 1.08 mg/g of barium.

Lead formate Pb(HCOO)$_2$ on Superlig 512-silica.

70 G of Superlig 512 (silica; 16.1 mmol macrocycle) was added to a solution of 71.75 g (1 mol) of lithium formate hydrate (HCOOLi.H$_2$O), 5 g (0.02 mol) of lead formate [Pb(HCOO)$_2$} and 4 ml (0.1 mol) of formic acid (HCOOH) in 1 l of water. This mixture was gently stirred during 24 h. The solid catalyst was filtered, washed with water (3*130 mol) and dried at 100° C. in a vacuum oven for 64 h. This resulted in a material containing 3.46 mg/g of lead.

Barium Bicarbonate Ba(HCO$_3$)$_2$ on Superlig 512-silica

Barium bicarbonate was immobilised in a three step procedure on the Superlig.

Step 1: 50 g of Superlig 512 (silica; 11.5 mmol macrocycle) was added to a solution of 4 g (19.2 mmol) of BaCl$_2$ in 200 ml of methanol. The mixture was stirred for two days at room temperature. The Superlig was filtered, washed with methanol and the solid was dries overnight in a vacuum oven. This resulted in a material containing 2.08 g (10 mmol) of $BaCl_2$.

Step 2: 3 g (40.5 mmol) of $NaHCO_3$ was dissolved in 140 ml of water and 130 ml of methanol. The $BaCl_2$/Superlig complex was added and the mixture was stirred at room temperature for 24 h. The mixture was filtered and washed with water.

Step 3: The partly exchanged complex (Superlig/$BaCl_2$—$Ba(HCO_3)_2$) was poured in a column and a solution of 4 g $NaHCO_3$ in 100 ml of water and 100 ml of methanol was passed over the Superlig (LHSV 1.1 l/l.h). The Superlig was washed with water and dried overnight in a vacuum oven. This resulted in a chlorine free material containing 2.54 g (9.8 mmol) of $Ba(HCO_3)_2$.

EO Batch Hydrolysis at 100° C.

The EO to MEG conversion was carried out as described above for examples 1–17 except that a water/EO molratio of 8.35 was used.

Recycle of Heterogeneous Catalyst

After completion of the EO batch hydrolysis the crude reaction mixture was cooled and the solid catalyst was filtered, washed with water (3×150 ml) and dried in a vacuum oven overnight.

The results are summarized in the following Table 2.

TABLE 2

| Example No. | Catalyst | Catalyst amount (mmol) | EO conversion (%) | MEG selectivity (%) |
|---|---|---|---|---|
| Comp. 17 | no catalyst; | — | 99.1 | 79.2 |
| Comp. 18 | barium formate [$Ba(HCOO)_2$] | 15 | 99.4 | 87.5 |
| 19 | Sup-S/$Ba(HCOO)_2$ | 5.5 | 99.5 | 88.1 |
| 20 | Sup-S/$Ba(HCOO)_2$ recycle from example 19 | | 99.6 | 85.8 |
| Comp. 21 | lead formate [$Pb(HCOO)_2$] | 15 | 99.3 | 82.7 |
| 22 | Sup-S/$Pb(HCOO)_2$ | 11.7 | 99.0 | 86.6 |
| 23 | Sup-S/$Pb(HCOO)_2$ recycle from example 22 | | 100 | 83.0 |
| 24 | Sup-S/$Ba(HCO_3)_2$ | 9.8 | 99.4 | 86.5 |
| 25 | Sup-S/$Ba(HCO_3)_2$ recycle from example 22 | | 99.1 | 88.7 |

What we claim is:

1. A process for the preparation of alkylene glycols by reacting an alkylene oxide with water in the presence of a catalytic composition comprising a macrocyclic chelating compound complexed with an ionic compound the anion of which is catalytically effective under the reaction conditions.

2. A process according to claim 1 characterized in that the macrocyclic chelating compound is selected from the groups of crown ethers and cryptands.

3. A process according to claim 2, characterized in that the anion is selected from the group of halogenides, carboxylates having from 1–20 carbon atoms, hydrogen carbonate, hydrogen sulphite, hydrogen phosphate and metalates.

4. A process according to claim 1, characterized in that the macrocyclic chelating compound is immobilised on or incorporated in an inert solid support material.

5. A process according to claim 4, characterized in that the support material is selected from the group consisting of inorganic oxides and organic polymers.

6. A process according to claim 5, characterized in that the support material is selected from the group consisting of silica, alumina, titania, zirconia, polystyrenes and polyacrylates.

7. A process according to claim 1, characterized in that the alkylene oxide is ethylene oxide and the alkylene glycol is ethylene glycol.

* * * * *